US006669687B1

(12) United States Patent
Saadat

(10) Patent No.: US 6,669,687 B1
(45) Date of Patent: Dec. 30, 2003

(54) APPARATUS AND METHODS FOR TREATING TISSUE

(76) Inventor: Vahid Saadat, 12679 Kane Dr., Saratoga, CA (US) 95070

(*) Notice: Subject to any disclaimer, the term of this patent is extended or adjusted under 35 U.S.C. 154(b) by 292 days.

(21) Appl. No.: 09/602,436

(22) Filed: Jun. 23, 2000

Related U.S. Application Data

(60) Provisional application No. 60/141,077, filed on Jun. 25, 1999.

(51) Int. Cl.[7] .............................................. A61B 18/18
(52) U.S. Cl. .............................. 606/14; 606/7; 606/15; 606/41; 606/49; 607/116; 607/122; 604/22; 604/916
(58) Field of Search ......................... 606/13–16, 27–29, 606/41, 45, 49–51, 159; 604/30, 20–22, 916; 607/115, 116, 119–122, 129–131; 623/2.1–2.4

(56) References Cited

U.S. PATENT DOCUMENTS

| 5,125,926 A | * | 6/1992 | Rudko et al. ................. 606/19 |
| 5,275,162 A | | 1/1994 | Edwards et al. |
| 5,281,218 A | | 1/1994 | Imran ........................... 606/41 |
| 5,336,252 A | | 8/1994 | Cohen |
| 5,443,446 A | | 8/1995 | Shturman |
| 5,454,807 A | * | 10/1995 | Lennox et al. ................ 606/15 |
| 5,492,119 A | | 2/1996 | Abrams |
| 5,673,695 A | * | 10/1997 | McGee et al. ............... 128/642 |
| 5,725,521 A | | 3/1998 | Mueller |
| 5,766,234 A | | 6/1998 | Chen et al. .................. 607/92 |
| 5,769,846 A | | 6/1998 | Edwards et al. .............. 606/41 |
| 5,827,203 A | | 10/1998 | Nita ............................... 601/2 |
| 5,827,268 A | | 10/1998 | Laufer .......................... 607/28 |
| 5,855,552 A | | 1/1999 | Houser et al. |
| 5,860,920 A | | 1/1999 | McGee et al. |
| 5,957,916 A | | 9/1999 | Jeevanandam et al. |
| 5,989,284 A | | 11/1999 | Laufer .......................... 607/96 |
| 5,997,534 A | * | 12/1999 | Tu et al. ....................... 606/41 |
| 6,004,269 A | | 12/1999 | Crowley et al. |
| 6,012,457 A | | 1/2000 | Lesh |
| 6,126,682 A | | 10/2000 | Sharkey et al. |
| 6,152,144 A | | 11/2000 | Lesh et al. |
| 6,283,962 B1 | * | 9/2001 | Tu et al. ....................... 606/41 |

FOREIGN PATENT DOCUMENTS

| WO | WO 98/35638 | | 8/1998 | |
| WO | 98/35638 | * | 8/1998 | ............. A61F/7/00 |
| WO | WO 99/02096 | | 1/1999 | |
| WO | WO 00/27292 | | 5/2000 | |

* cited by examiner

*Primary Examiner*—Linda C. M. Dvorak
*Assistant Examiner*—Ahmed M. Farah
(74) *Attorney, Agent, or Firm*—Morrison & Foerster LLP

(57) ABSTRACT

Apparatus and methods are provided for thermally or mechanically treating tissue, such as valvular structures, to reconfigure or shrink the tissue in a controlled manner, thereby improving or restoring tissue function. The apparatus comprises a catheter in communication with an end effector. The end effector induces a temperature rise in an annulus of tissue surrounding the leaflets of a valve sufficient to cause shrinkage of the tissue, thereby reducing a diameter of the annulus and causing the valves to close more tightly. Alternatively, the end effector selectively induces a temperature rise in the chordae tendineae sufficient to cause a controlled degree of shortening of the chordae tendineae, thereby enabling the valve leaflets to be properly aligned. In another alternative, the end effector is configured to mechanically shorten the effective length of the chordae tendineae by forcing the tendineae through a tortuous path, again properly aligning the valve leaflets.

48 Claims, 15 Drawing Sheets

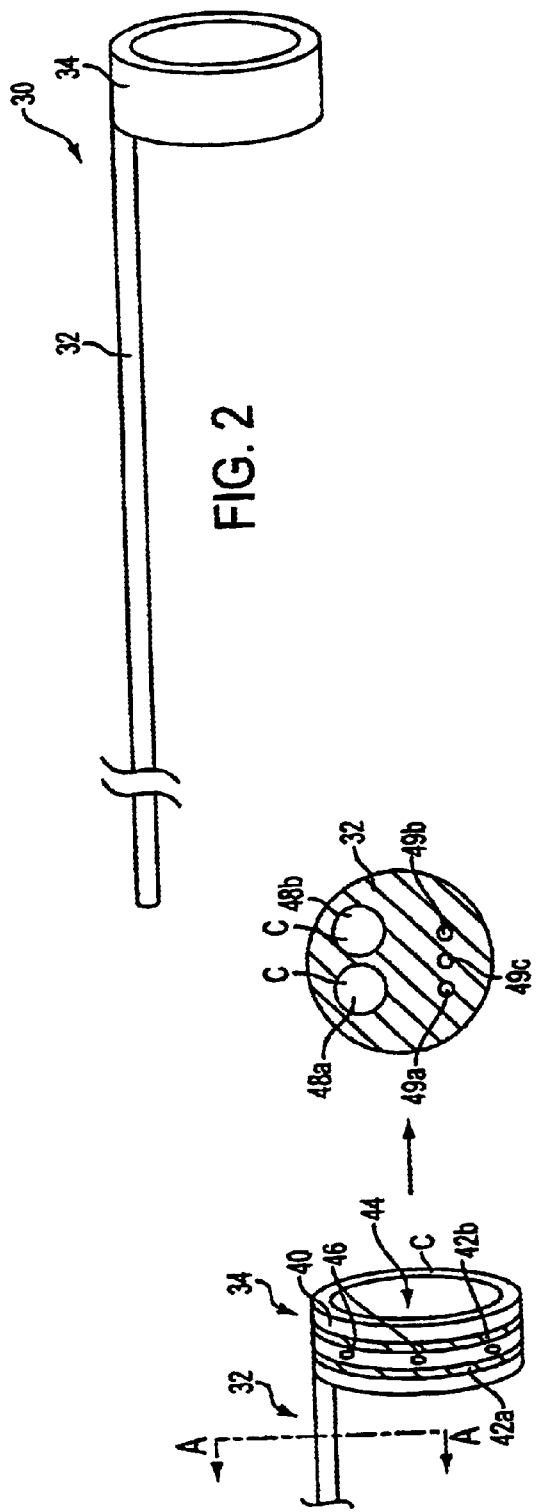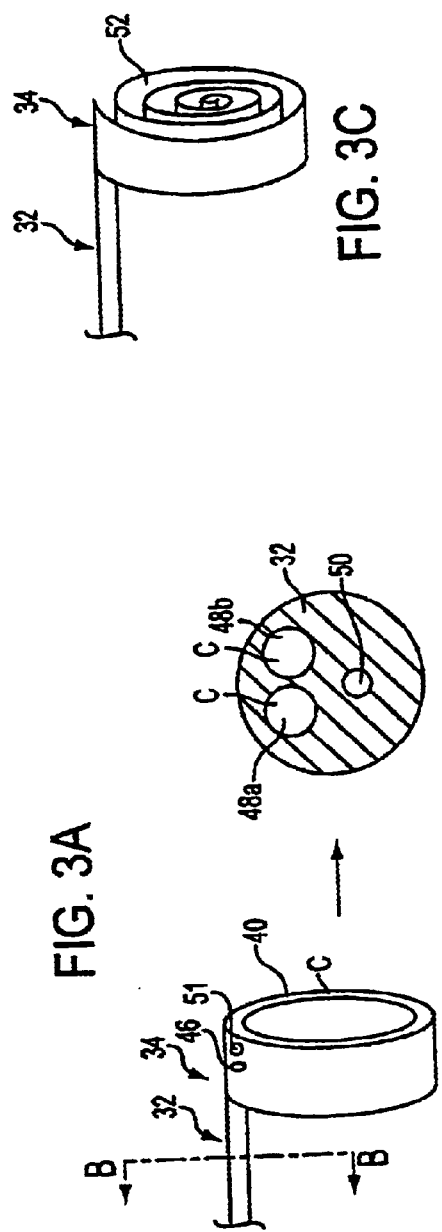

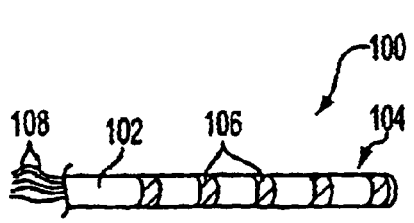
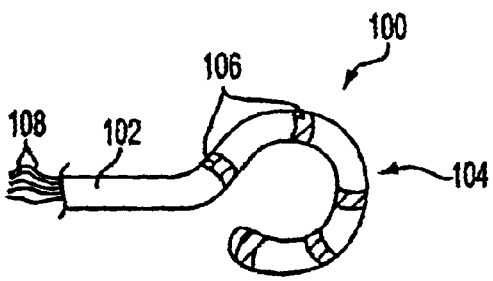
FIG. 8A          FIG. 8B
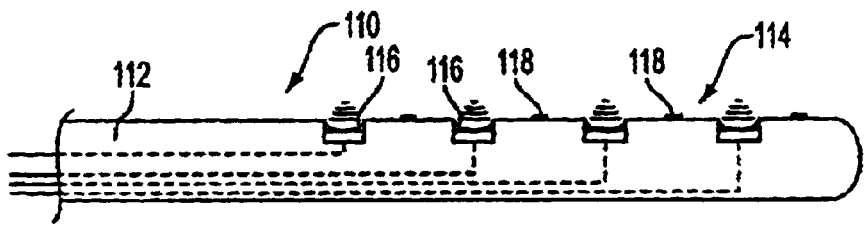
FIG. 9
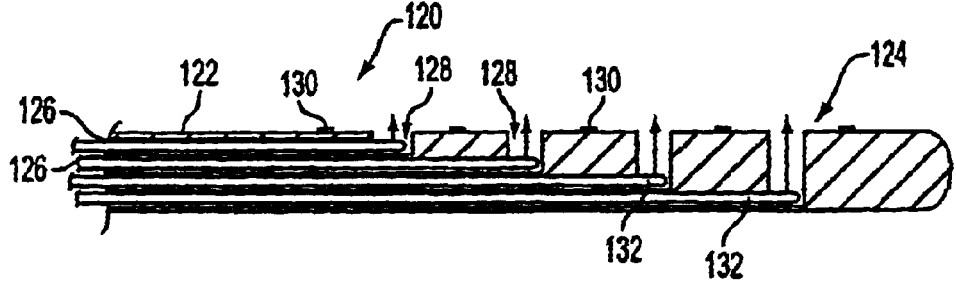
FIG. 10
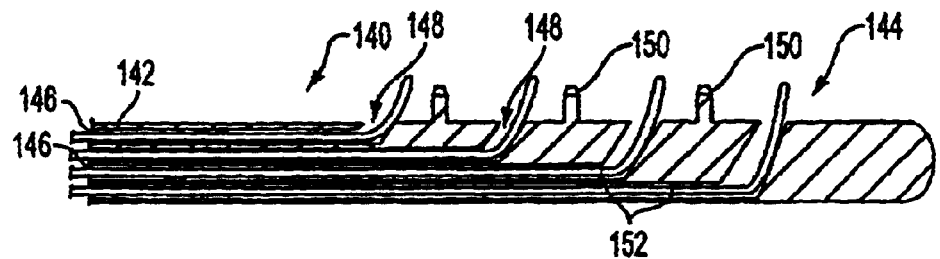
FIG. 11

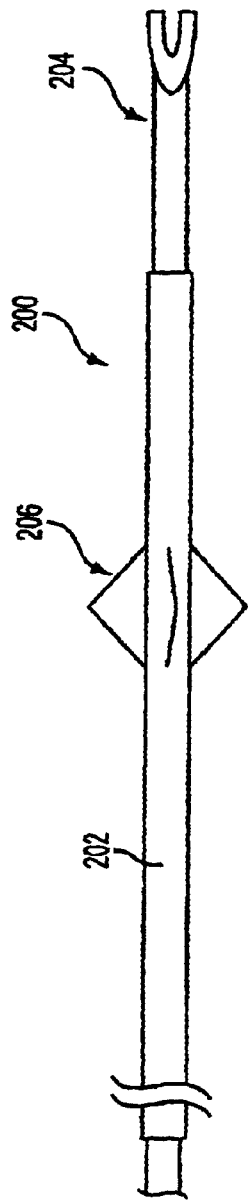
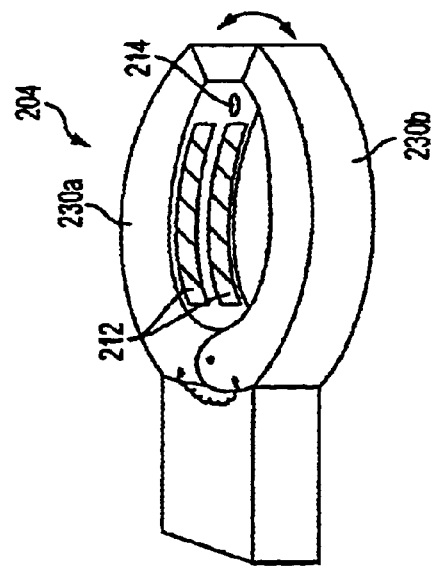
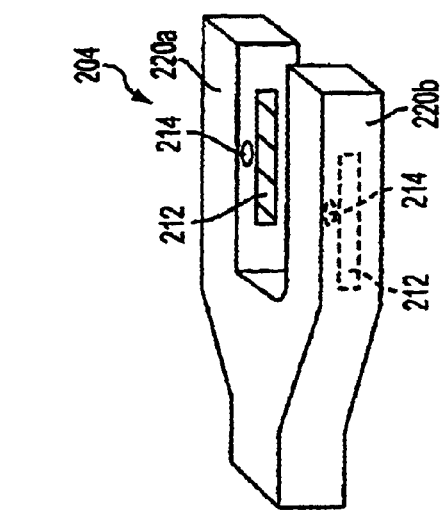
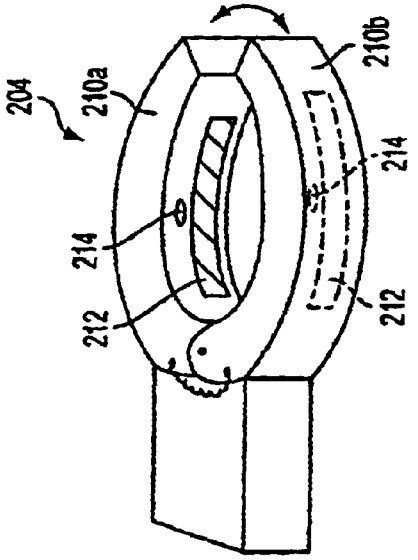

APPARATUS AND METHODS FOR TREATING TISSUE

REFERENCE TO RELATED APPLICATIONS

The present application claims benefit from the filing date of provisional U.S. patent application Ser. No. 60/141,077 filed Jun. 25, 1999.

FIELD OF THE INVENTION

The present invention relates to treatment of tissue. More particularly, the present invention provides methods and apparatus for treating valvular disease with a catheter inserted into a patient's cardiac chambers, the catheter having an end effector for modifying cardiac structures, including valve leaflets and support structure.

BACKGROUND OF THE INVENTION

Degenerative valvular disease is the most common cause of valvular regurgitation in human beings. Regurgitation is typically characterized by an expanded valve annulus or by lengthened chordae tendineae. In either case, an increase in the geometry of a valve or its supporting structure causes the valve to become less effective, as it no longer fully closes when required.

Loose chordae tendineae may result, for example, from ischemic heart disease affecting the papillary muscles. The papillary muscles attach to the chordae tendineae and keep the leaflets of a valve shut. Some forms of ischemic cardiac disease cause the papillary muscles to lose their muscle tone, resulting in a loosening of the chordae tendineae. This loosening, in turn, allows the leaflets of the affected valve to prolapse, causing regurgitation.

It therefore would be desirable to provide methods and apparatus for treatment of tissue that modify the geometry and operation of a heart valve.

It would also be desirable to provide methods and apparatus that are configured to thermally treat chordae tendineae, the annulus of a valve, or valve leaflets.

SUMMARY OF THE INVENTION

In view of the foregoing, it is an object of the present invention to provide methods and apparatus for the treatment of tissue that modify the geometry and operation of a heart valve.

It is another object of the present invention to provide methods and apparatus that are configured to thermally treat chordae tendineae, the annulus of a valve, or valve leaflets.

These and other objects of the present invention are accomplished by providing apparatus and methods for thermally or mechanically treating tissue, such as valvular structures, to reconfigure or shrink the tissue in a controlled manner, thereby improving or restoring tissue function. Embodiments of the present invention advantageously may be employed to modify flow regulation characteristics of a cardiac valve or its component parts, as well as to modify flow regulation in other lumens of the body, including, for example, the urinary sphincter, digestive system valves, leg vein valves, etc., where thermal shrinkage or mechanical reconfiguration of tissue may provide therapeutic benefit.

In a first family of embodiments of the present invention, apparatus is provided having an end effector that induces a temperature rise in an annulus of tissue surrounding the leaflets of a valve sufficient to cause shrinkage of the tissue, thereby reducing a diameter of the annulus and causing the valves to close more tightly. In a second family of embodiments, apparatus is provided having an end effector that selectively induces a temperature rise in the chordae tendineae sufficient to cause a controlled degree of shortening of the chordae tendineae, thereby enabling the valve leaflets to be properly aligned. In yet a third family of embodiments, apparatus is provided having an end effector comprising a mechanical reconfigurer configured to attach to a longitudinal member, such as the chordae tendineae. The reconfigurer forces the longitudinal member into a tortuous path and, as a result, reduces the member's effective overall or straight length.

Any of these embodiments may employ one or more expanding members that serve to stabilize the end effector in contact with the tissue or structure to be treated. In addition, where it is desired to preserve the interior surface of a lumen or structure, the instrument may include means for flushing the surface of the tissue with cooled saline. Where it is desired to achieve a predetermined degree of heating at a depth within a tissue or structure, the end effector may comprise a laser having a wavelength selected to penetrate tissue to the desired depth, or the end effector may comprise a plurality of electrically conductive needles energized by an RF power source, as is known in the electrosurgical arts. The end effector may alternatively comprise an acoustic heating element, such as an ultrasonic transducer.

Methods of using apparatus according to the present invention are also provided.

BRIEF DESCRIPTION OF THE DRAWINGS

The above and other objects and advantages of the present invention will be apparent upon consideration of the following detailed description, taken in conjunction with the accompanying drawings, in which like reference numerals refer to like parts throughout, and in which:

FIG. 2 is a side view of apparatus of a first family of embodiments constructed in accordance with the present invention;

FIGS. 3A–3C are, respectively, a side view of an end effector for use with the apparatus of FIG. 2 and a sectional view through its catheter along sectional view line A—A, a side view of an alternative end effector and a sectional view of its catheter along view line B—B, and a side view of a still further alternative end effector;

FIGS. 8A and 8B are side views of another alternative embodiment of the apparatus of FIG. 6 having multipolar, individual electrodes;

FIG. 9 is a side view of an alternative embodiment of the apparatus of FIG. 8 having individual ultrasonic transducers;

FIG. 10 is a side-sectional view of another alternative embodiment of the apparatus of FIG. 8 having individual laser fibers;

FIG. 11 is a side-sectional view of an alternative embodiment of the apparatus of FIGS. 8–10 having individual barb members that may comprise multipolar electrodes, ultrasonic transducers, or laser fibers;

FIG. 16 is a top view of apparatus of a second family of embodiments constructed in accordance with the present invention;

FIGS. 17A–17C are views of end effectors for use with the apparatus of FIG. 16;

DETAILED DESCRIPTION OF THE INVENTION

Figure 1:
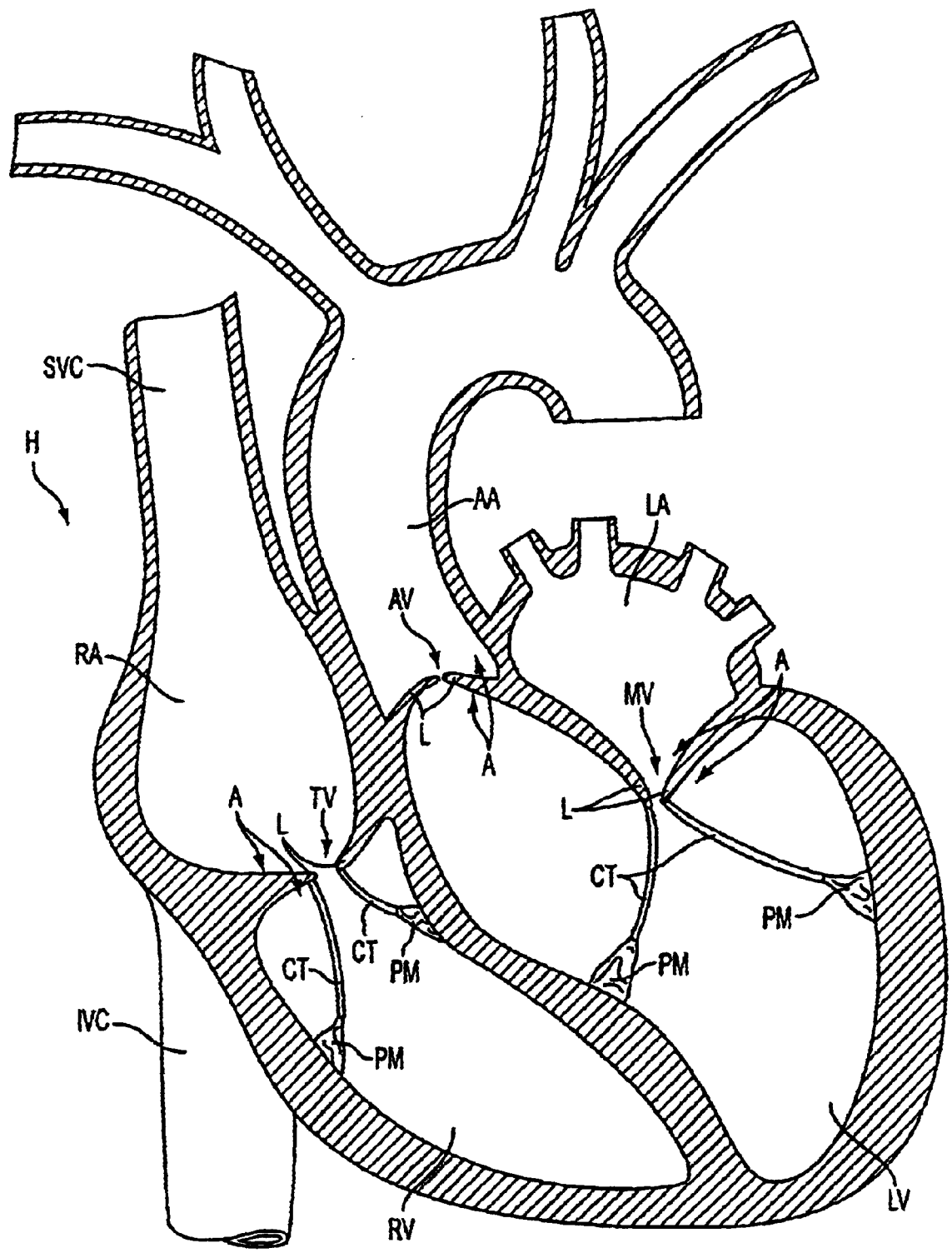
FIG. 1 is a side-sectional view of a human heart showing major structures of the heart, including those pertaining to valvular degeneration.

With reference to FIG. 1, a sectional view through human heart H is presented. Major structures labeled include the right atrium RA, left atrium LA, right ventricle RV, left ventricle LV, superior vena cava SVC, inferior vena cava IVC, and ascending aorta AA. Structures that may be involved in valvular degeneration and regurgitation are also labeled, including the papillary muscles PM, chordae tendineae CT, valve leaflets L, and annuluses of tissue surrounding the leaflets A, as well as the tricuspid valve TV, the bicuspid or mitral valve MV, and the aortic valve AV. The pulmonary valve PV is not seen in the cross section of FIG. 1, but may also experience valvular degeneration. As discussed previously, degenerative valvular disease often leads to valvular regurgitation, which is typically characterized by an expanded valve annulus A or by lengthened chordae tendineae CT. Loose chordae tendineae may result from ischemic heart disease affecting the papillary muscles PM, which attach to the chordae tendineae and act to regulate flow through leaflets L.

The present invention therefore provides apparatus and methods for shrinking or reconfiguring tissue, such as annulus A or chordae tendineae CT. Embodiments of the present invention advantageously may be employed to modify flow regulation characteristics of a cardiac valve or its component parts, as well as to modify flow regulation in other lumens of the body, including, for example, the urinary sphincter, digestive system valves, leg vein valves, etc., where thermal shrinkage or mechanical reconfiguration of tissue may provide therapeutic benefit.

FIGS. 2–15 illustrate apparatus of a first family of embodiments of the present invention. The first family of embodiments have an end effector that induces a temperature rise in an annulus of tissue surrounding the leaflets of a valve sufficient to cause shrinkage of the tissue, thereby reducing a diameter of the annulus and causing the valve to close more tightly.

Referring to FIG. 2, apparatus 30 comprises catheter 32 having end effector 34 in a distal region of the catheter. End effector 34 may be collapsible within and extendable beyond the distal end of catheter 30 to permit percutaneous delivery to a treatment site. End effector 34 has an annular shape to facilitate treatment of an annulus of tissue, as well as stabilization against the walls of a treatment site.

With reference to FIGS. 3A–3C, alternative embodiments of end effector 34 and catheter 32 are described. In FIG. 3A, end effector 34 comprises expandable balloon 40. Balloon 40 comprises bipolar electrodes 42a and 42b that may be attached to a radiofrequency ("RF") voltage or current source (not shown). Balloon 40 further comprises lumen 44 to facilitate unimpeded blood flow or fluid transport therethrough, and temperature sensors 46 to monitor shrinkage of tissue caused by current flow between bipolar electrodes 42a and 42b. Sensors 46 may comprise, for example, standard thermocouples, or any other temperature sensor known in the art.

The end effector of FIG. 3A is thus capable of achieving controlled luminal shrinkage while allowing blood to pass through the center of balloon 40. Electrodes 42a and 42b are disposed as bands on the periphery of balloon 40 and may inject an RF electrical current into the wall of a treatment site, such as an annulus or lumen, to shrink collagen contained therein. Furthermore, balloon 40 may be inflated with a circulating coolant C, such as water, to cool the surface of balloon 40 and thereby minimize thermal damage at the surface of the treatment site. Thermally damaged tissue may be thrombogenic and may form thrombus on its surface, leading to potentially lethal complications.

FIG. 3A also provides a cross section through an embodiment of catheter 32, along sectional view line A—A, for use in conjunction with the balloon embodiment of end effector 34. Catheter 32 comprises coolant lumens 48a and 48b that may circulate coolant C into and out of balloon 40, respectively. It further comprises wires 49a–49c, electrically coupled to electrode 42a, electrode 42b, and temperature sensors 46, respectively.

In FIG. 3B, an alternative embodiment of end effector 34 and catheter 32 is presented. Instead of RF energy, the heating element in this embodiment is a laser source (not shown) coupled to fiber optic cable 50 having side firing tip 51. The laser source injects light energy into the wall of a treatment site via fiber optic cable 50, thereby thermally shrinking the tissue. The wavelength of the laser may be selected to penetrate tissue to a desired depth. Furthermore, a plurality of fiber optic cables 50, coupled to the laser source and disposed about the circumference of balloon 40, may be provided.

Balloon 40 is substantially transparent to the laser energy, and coolant C may again serve to cool the surface of balloon 40, thereby minimizing damage at the surface of the treatment site. The circulating stream of coolant C maintains the temperature of surface tissue layers at a sufficiently low level to prevent thermal damage, and thus, to prevent formation of thrombus. Temperature sensor 46 optionally may also be provided.

As seen in FIG. 3C, end effector 34 may alternatively comprise wrapped sheet 52 incorporating one or more electrodes on its surface. Sheet 52 may be advanced to a treatment site in a collapsed delivery configuration within a lumen of catheter 32, and may then be unfurled to an expanded deployed configuration wherein it contacts the interior wall of the treatment site and may be energized to shrink tissue.

Figure 4:
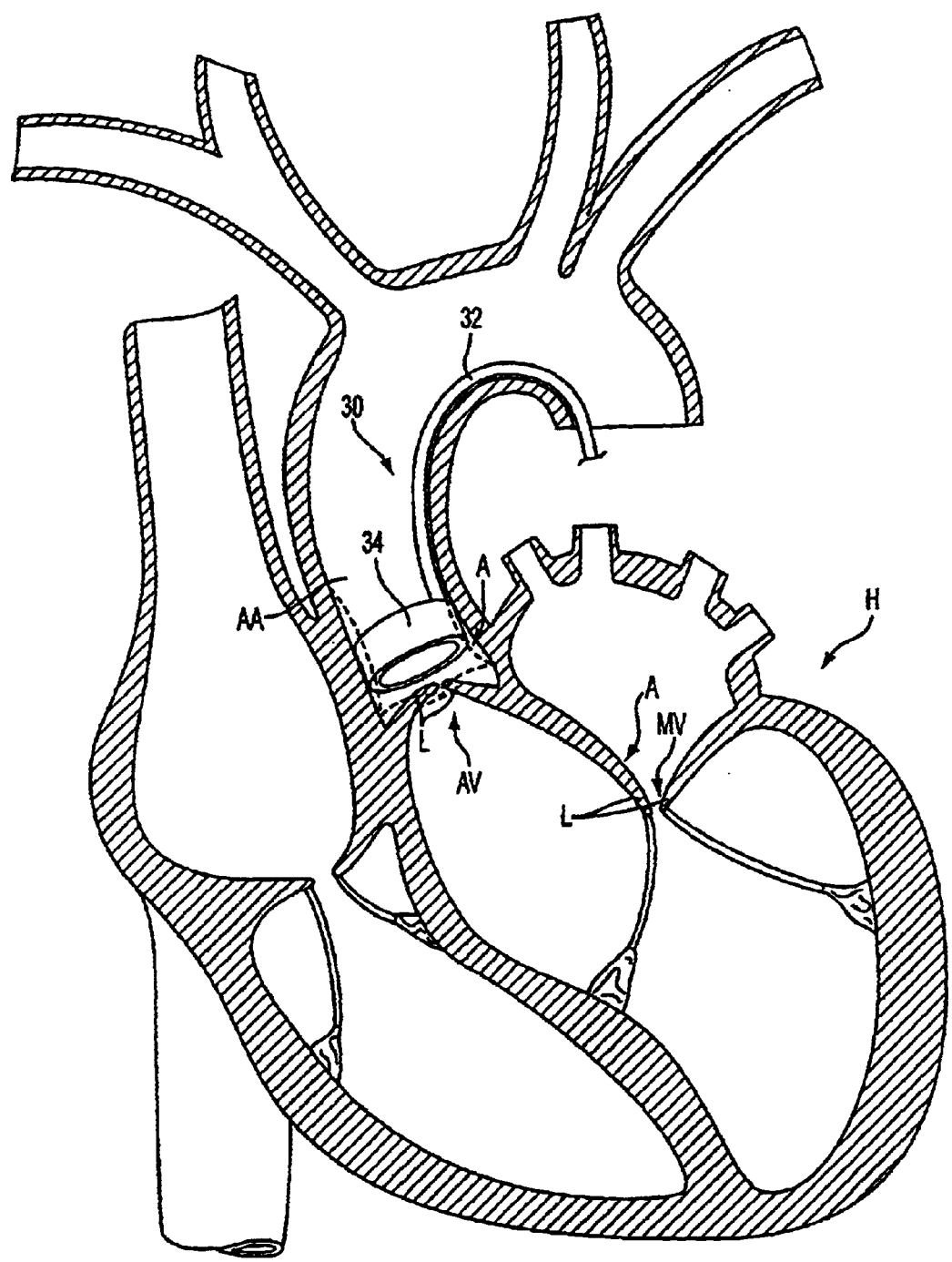
FIG. 4 is a sectional view through the human heart, depicting a method of using the apparatus of FIG. 2 to shrink tissue in an annulus surrounding the leaflets of a regurgitating valve.

Referring now to FIG. 4, a method of using apparatus 30 to thermally shrink an annulus of tissue is described. End effector 34 is placed in intimate contact with the inner wall of a blood vessel or other body lumen. In the valvular regurgitation treatment technique of FIG. 4, end effector 34 is percutaneously delivered just proximal of aortic valve AV within ascending aorta AA at annulus of tissue A supporting leaflets L, using well-known techniques. Aortic valve AV suffers from valvular degeneration, leading to regurgitation. End effector 34 delivers energy to annulus A sufficient to heat and shrink the annulus, thus enhancing function of the degenerative valve. Collagen within annulus A shrinks and reduces a diameter of the annulus. Leaflets L are approximated towards one another, as seen in dashed profile in FIG. 4, and valvular regurgitation is reduced or eliminated. In addition to valvular regurgitation, the technique is expected to effectively treat aortic insufficiency.

End effector 34 stabilizes apparatus 30 against the wall of a body passageway. Once stabilized, a source of energy may be applied to the wall to thermally shrink the tissue contained in the wall. In addition to the application of FIG. 4, treatment may be provided, for example, to the annulus of mitral valve MV, to the urinary sphincter for treatment of incontinence, to digestive system valves for treatment of acid reflux, to leg vein valves, and to any other annulus of tissue where treatment is deemed beneficial.

Figure 5A:
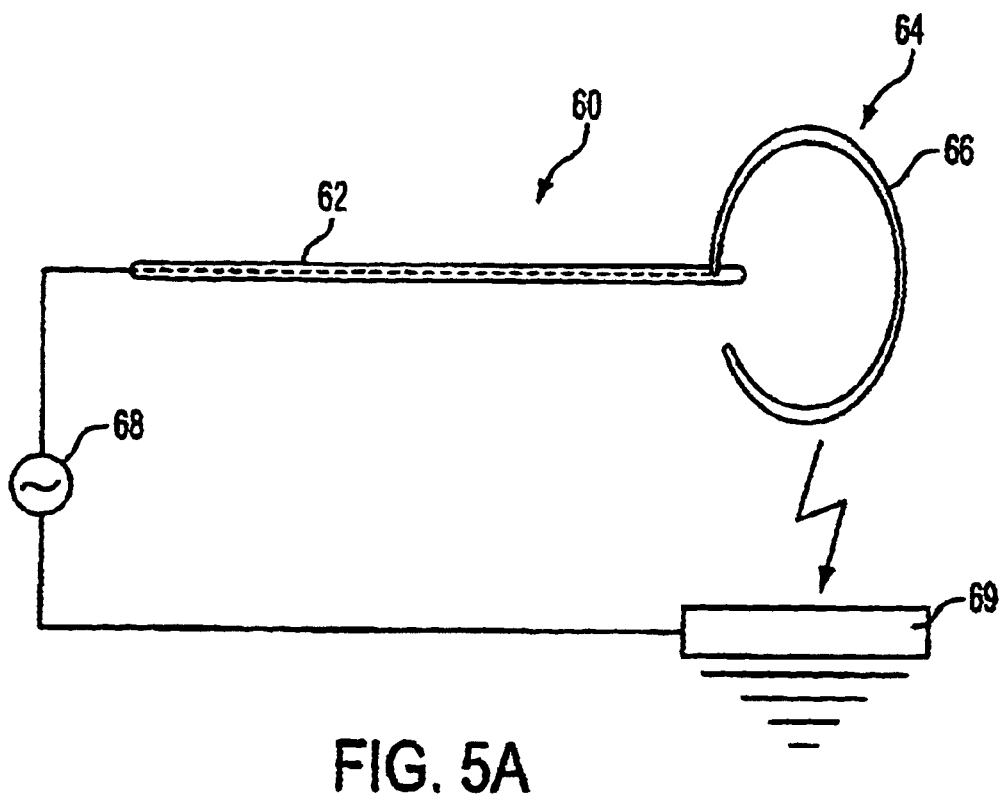
FIGS. 5A and 5B are schematic views of alternative embodiments of the apparatus of FIG. 2.
Figure 5B:
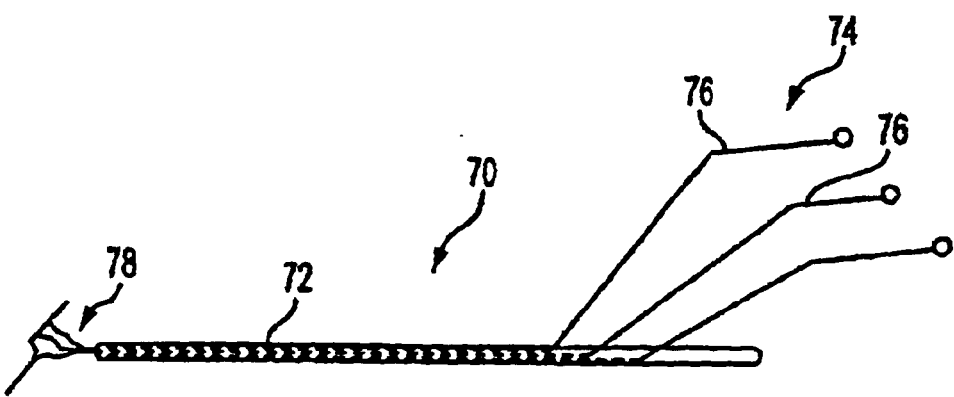

With reference to FIGS. 5A and 5B, alternative embodiments of the apparatus of FIG. 2 are described. In FIG. 5A, apparatus 60 comprises catheter 62 having a lumen, in which end effector 64 is advanceably disposed. End effector 64 comprises monopolar electrode 66, which is fabricated in an arc from a shape memory alloy, such as spring steel or nitinol, to approximate the shape of an annulus of tissue at a treatment site within a patient. Electrode 66 may be retracted within the lumen of catheter 62 to facilitate transluminal, percutaneous delivery to the treatment site. Once in position, electrode 66 may be advanced out of a distal region of catheter 62. The electrode resumes its arc shape and approximates the wall of the treatment site.

Monopolar electrode 66 is electrically coupled to RF source 68, which is positioned outside of the patient. RF source 68 is, in turn, coupled to reference electrode 69. When RF source 68 is activated, current flows between monopolar electrode 66 and reference electrode 69, which may, for example, be attached to the exterior of the patient in the region of the treatment site. RF current flows into the wall of the treatment site, thereby effecting annular tissue shrinkage, as described previously.

In FIG. 5B, a bipolar embodiment is provided. Apparatus 70 comprises catheter 72 and end effector 74. End effector 74 comprises a plurality of atraumatic tipped legs 76 that are electrically coupled by a plurality of current carrying wires 78 to an RF source (not shown). The plurality of legs contact the wall of a treatment site and inject current into the wall. The current flows between the tips of the legs. Alternatively, the plurality of legs may comprise a monopolar electrode coupled by a single wire to the RF source, and current may flow between the plurality of legs and a reference electrode, as in FIG. 5A.

Figure 6A:
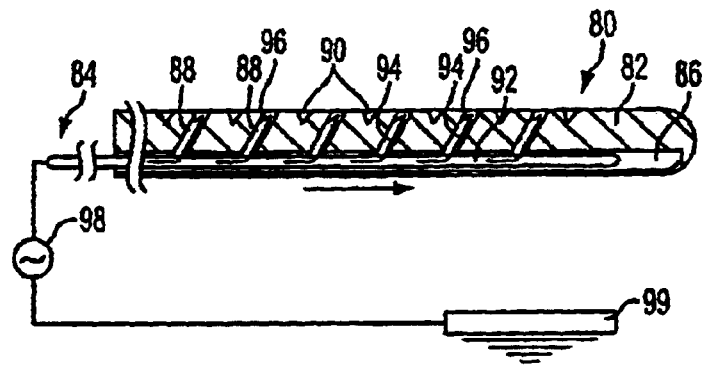
FIGS. 6A–6D are views of a still further alternative embodiment of the apparatus of FIG. 2 having barbs, and illustrating a method of use.
Figure 6B:
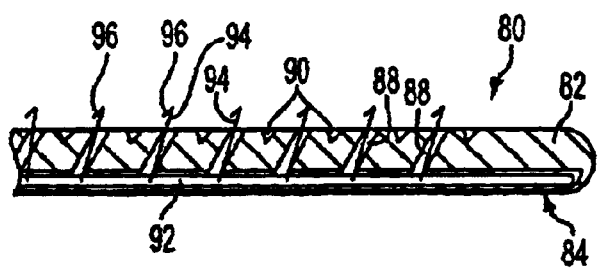

Referring to FIGS. 6A–6D, another alternative embodiment of the apparatus of FIG. 2 is described. FIG. 6A shows apparatus 80 in side-sectional view in a retracted delivery configuration. Apparatus 80 comprises catheter 82 and end effector 84. Catheter 82 further comprises central bore 86, a plurality of side bores 88, and optional temperature sensors 90. End effector 84 may, for example, be fabricated from nitinol or spring steel, and comprises conductive shaft 92 having a plurality of radially extending electrodes 94 with optional barbs 96. Conductive shaft 92 is electrically coupled to RF source 98, which is electrically coupled to reference electrode 99. Conductive shaft 92 is disposed within central bore 86, while electrodes 94 are disposed within side bores 88.

End effector 84 is advanceable with respect to catheter 82. When advanced distally, apparatus 80 assumes the expanded deployed configuration of FIG. 6B, wherein electrodes 94 extend through side bores 88 beyond the surface of catheter 82. Apparatus 80 is also configured such that its distal region may approximate the shape of an annulus of tissue, as described hereinbelow with respect to FIG. 6D, and is thus suited for both linear and circular subsurface tissue coagulation and shrinkage.

Figure 6C:
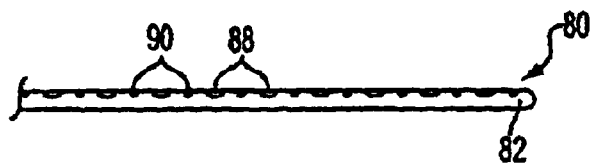
Figure 6D:
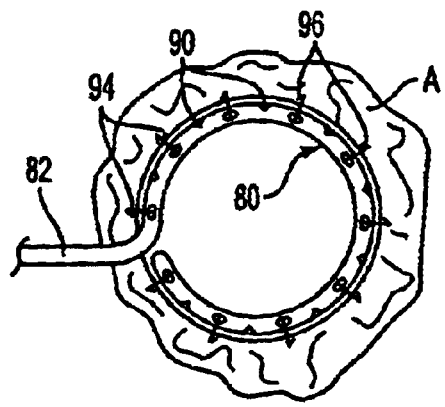

FIGS. 6C and 6D provide a method of using apparatus 80 to treat annulus of tissue A surrounding a heart valve. Apparatus 80 is percutaneously advanced to the surface of a heart valve in the delivery configuration of FIG. 6C. Once positioned at annulus A, the distal region of apparatus 80 approximates the shape of the annulus, as seen in FIG. 6D. This may be accomplished, for example, with a steering mechanism comprising two purchase points or a pre-shaped tip that is retracted within a straight guiding catheter to allow insertion into the vascular system, as described in U.S. Pat. No. 5,275,162, which is incorporated herein by reference. Once inserted, the pre-shaped tip is advanced out of the guide catheter and recovers its preformed shape.

With apparatus 80 approximating annulus A, end effector 84 is distally advanced with respect to catheter 82, thereby selectively advancing electrodes 94 into the annulus. RF source 98 then provides RF current, which flows between electrodes 94 and reference electrode 99. The annulus of tissue shrinks, bringing valve leaflets into proper position and minimizing or eliminating regurgitation through the valve.

Catheter 82 insulates conductive shaft 92 from annulus A, thereby protecting surface tissue and only allowing coagulation at depth in treatment zones surrounding electrodes 94. To further ensure that coagulation only occurs at depth, a coolant, such as saline, may be introduced through central bore 86 and side bores 88 of catheter 82 to the surface of annulus A, thereby cooling and flushing the area where electrodes 94 penetrate the tissue. It is expected that such liquid infusion will keep the surface of the annulus clean and will prevent thrombus formation in response to thermal damage.

Figure 7A:
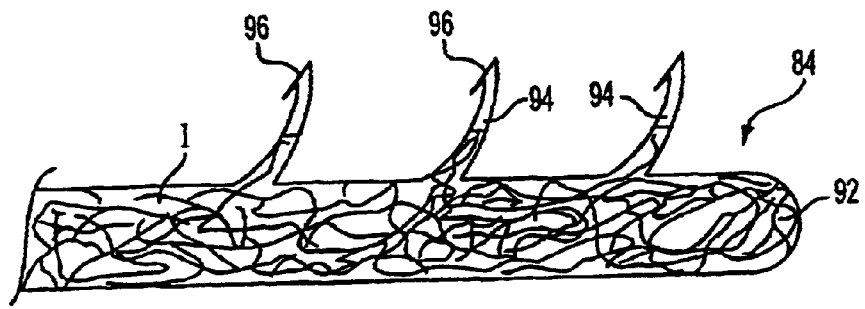
FIGS. 7A–7C are schematic views showing, respectively, an alternative embodiment of the end effector of FIGS. 6 having electrically insulated barbs, a method of using the end effector to thermally treat tissue, and a temperature profile within the tissue during treatment.
Figure 7B:
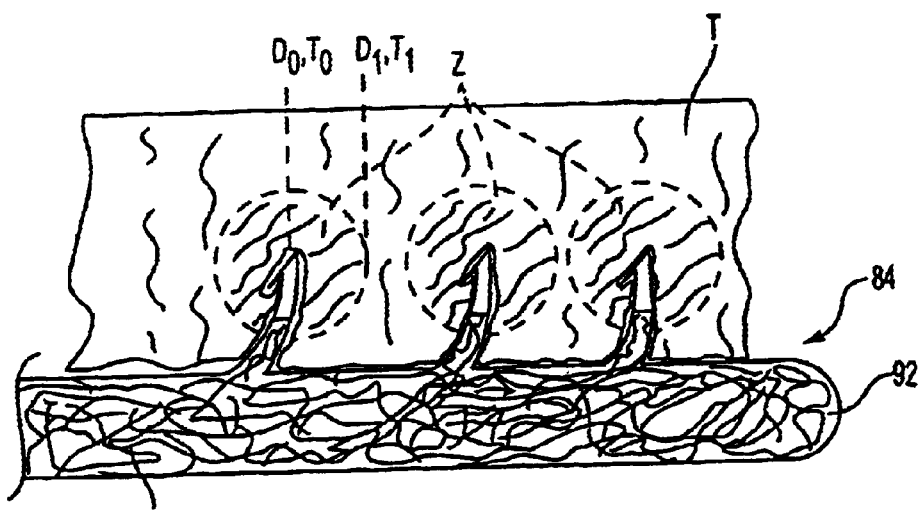
Figure 7C:
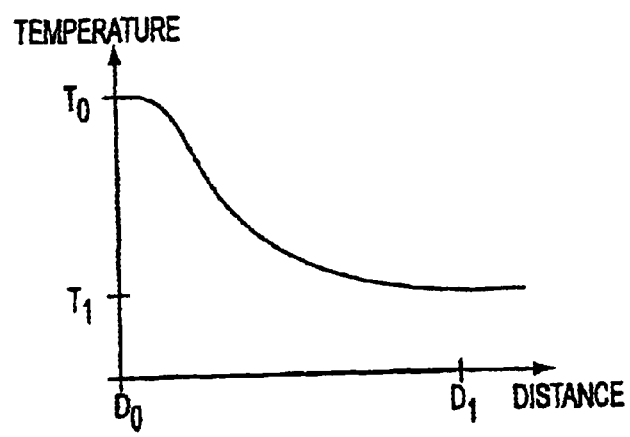

Referring now to FIGS. 7A–7C, an alternative embodiment of end effector 84 of FIGS. 6 is described. The end effector of FIGS. 7 is equivalent to the end effector of FIGS. 6 except that it is coated with electrically insulating layer I. Insulation layer I covers the entire exterior of end effector 84, except at the distal ends of the plurality of electrodes 94. The layer is preferably sufficiently thin to allow insertion of electrodes 94 into tissue T without impediment. The exposed distal ends of the electrodes are configured to deliver energy into subsurface tissue at treatment zones Z. The zones may be ideally modeled as spheres of subsurface tissue. Tissue shrinks within treatment zones Z without damaging surface tissue, as seen in FIG. 7B.

The size of treatment zones Z may be controlled to ensure that tissue remodeling only occurs at depth. Assuming a temperature $T_1$, at which tissue damage is negligible, the magnitude of current passed through tissue T may be selected (based on the material properties of the tissue and the depth of insertion of electrodes 94 within the tissue) such that the temperature decays from a temperature $T_0$ at a position $D_0$ at the surface of an electrode 94 to the benign temperature $T_1$ at a distance $D_1$ from the surface of the electrode. The distance $D_1$ may be optimized such that it is below the surface of tissue T. An illustrative temperature profile across a treatment zone Z is provided in FIG. 7C.

With reference to FIGS. 8A and 8B, another alternative embodiment of the apparatus of FIG. 6 is described. Apparatus 100 comprises catheter 102 and end effector 104. End effector 104 further comprises a plurality of individual, multipolar electrodes 106, which are electrically coupled to an RF or other current source (not shown) by a plurality of current carrying wires 108. As with the embodiments of FIGS. 6 and 7, apparatus 100 is configured such that end effector 104 may approximate an annulus, as seen in FIG. 8B.

Referring to FIGS. 9–11, alternative embodiments of the apparatus of FIGS. 8 are described. In FIG. 9, apparatus 110 comprises catheter 112 and end effector 114. End effector 114 comprises a plurality of acoustic heating elements 116. Acoustic elements 116 may, for example, comprise ultrasonic transducers. The acoustic energy may further be focused by appropriate means, for example, by lenses, such that a tissue damage threshold sufficient to cause shrinkage is only attained at a specified depth within treatment site tissue, thereby mitigating surface tissue damage and thrombus formation. Acoustic elements 116 are connected to appropriate controls (not shown). Apparatus 110, and any other apparatus described herein, may optionally comprise temperature sensors 118.

In FIG. 10, apparatus 120 comprises catheter 122 and end effector 124. Catheter 122 comprises a plurality of central bores 126 and a plurality of side bores 128, as well as a plurality of optional temperature sensors 130. End effector 124 comprises a plurality of side-firing fiber optic laser fibers 132 disposed within central bores 126 of catheter 122. The fibers are aligned such that they may deliver energy through side bores 128 to heat and induce shrinkage in target tissue. Fibers 132 are coupled to a laser source (not shown), as discussed with respect to FIG. 3B. Suitable wavelengths for the laser source preferably range from visible (488–514 nm) to infrared (0.9–10.6 microns), wherein each wavelength has an ability to heat tissue to a predetermined depth. As an example, a preferred laser source comprises a continuous wave laser having a 2.1 micron wavelength, which will shrink and heat tissue to a depth of 1–2 mm.

In FIG. 11, apparatus 140 comprises catheter 142 and end effector 144. Catheter 132 comprises central bores 146 and side bores 148. Catheter 132 further comprises temperature sensors 150 that are configured to penetrate superficial tissue layers to measure temperature at depth. Temperature sensors 150 may be retractable and extendable to facilitate percutaneous delivery of apparatus 140. End effector 144 comprises fibers 152 disposed within central bores 146. Fibers 152 are retractable within and extendable beyond side bores 148. Fibers 152 are preferably sharpened to facilitate tissue penetration and energy delivery to subsurface tissue, thereby inducing shrinkage of the tissue.

Fibers 152 may comprise any of a number of energy delivery elements. For example, fibers 152 may comprise a plurality of optical fibers coupled to a laser (not shown). The wavelength of the laser may be selected as described hereinabove, while the energy deposited by the fibers may be controlled responsive to the temperature recorded by sensors 150. Thus, for example, a controller (not shown) may be provided to switch off the laser once a preset temperature, for example, 45° C.–75° C., is attained, thereby ensuring that a sufficiently high temperature is achieved to cause tissue shrinkage without inadvertently damaging surrounding tissues.

Fibers 152 may alternatively comprise a plurality of multipolar electrodes. Each electrode may be capable of injecting RF energy into tissue independently. Alternatively, current may be passed between a pair of adjacent or non-adjacent electrodes to heat intervening tissue.

Figure 12:
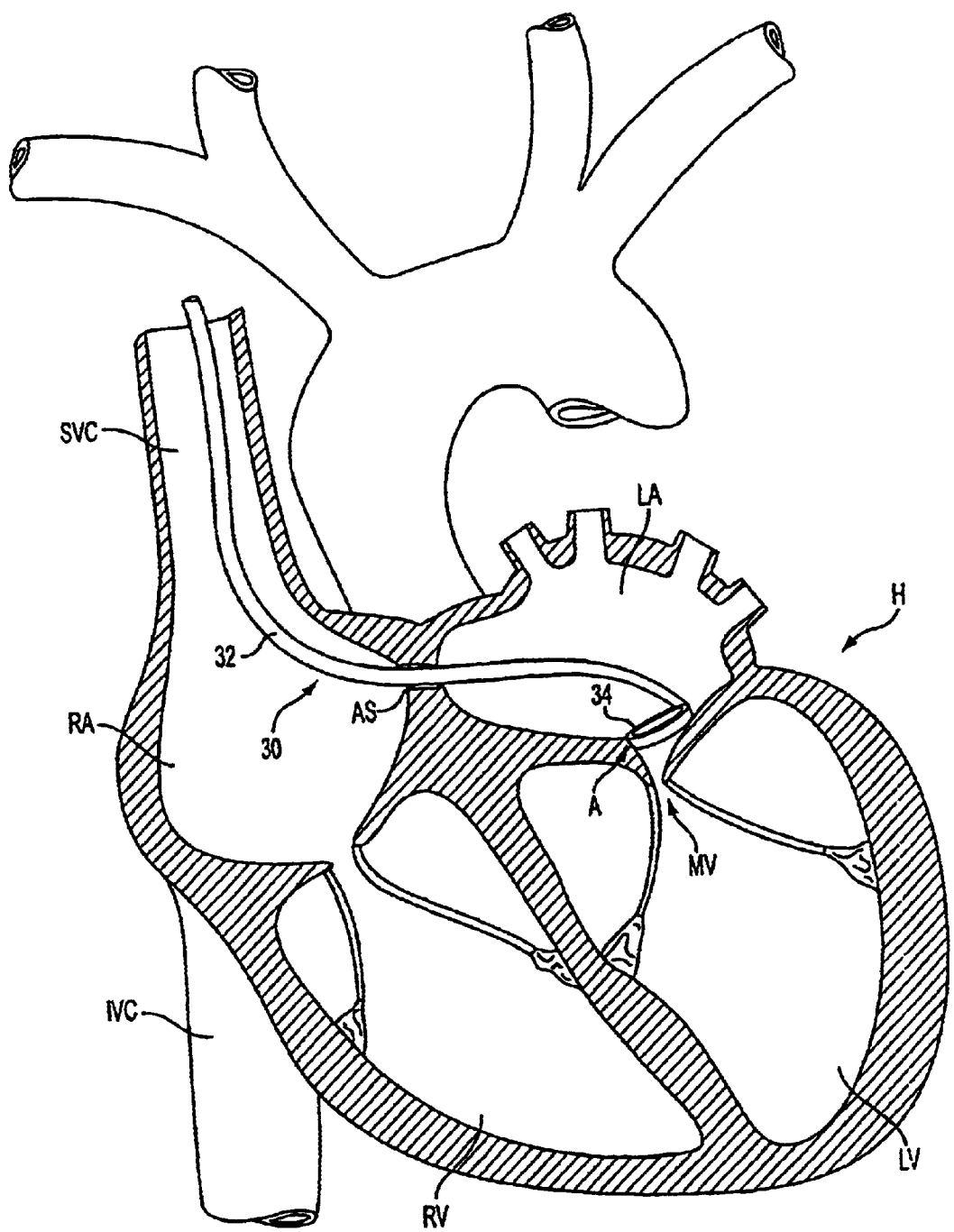
FIG. 12 is a sectional view through the human heart, illustrating an alternative method of introducing apparatus of the first family of embodiments to a treatment site.

Referring now to FIG. 12, an alternative method of introducing apparatus of the first family of embodiments to a treatment site is described. Apparatus 30 of FIG. 2 is been introduced to the annulus of tissue A surrounding mitral valve MV via the venous circulatory system. Catheter 32 is transluminally inserted via the jugular vein and superior vena cava SVC. The distal end of the catheter or a separate instrument then penetrates atrial septum AS using a procedure known as septostomy. Once the septum is perforated, end effector 34 may be inserted into left atrium LA and positioned over mitral valve annulus A to effect the thermal treatment described hereinabove. The tricuspid valve in the right ventricle, and the pulmonic valve, may also be treated in the same manner using a venous approach.

Figure 13A:
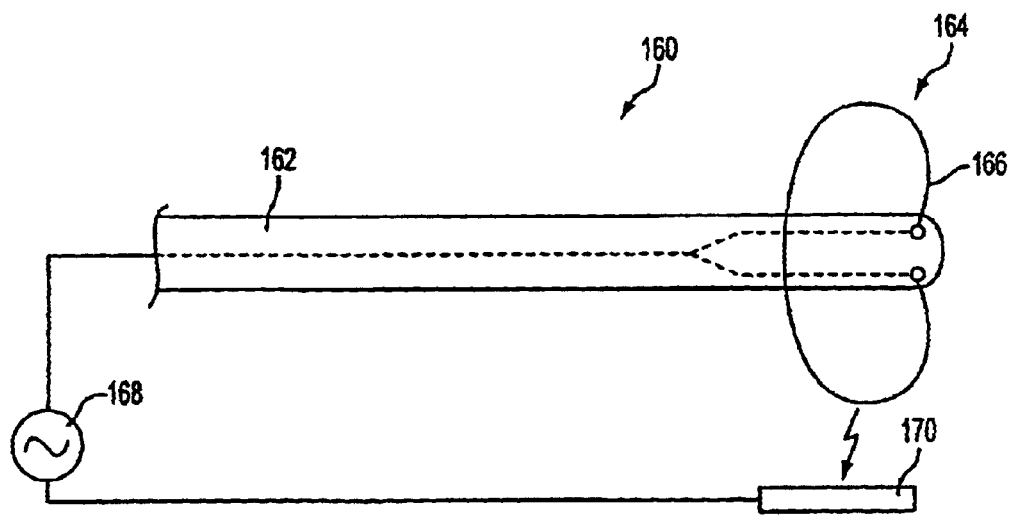
FIGS. 13A and 13B are views of an alternative embodiment of the apparatus of FIG. 2 shown, respectively, in schematic side view and in use shrinking an annulus of tissue.
Figure 13B:
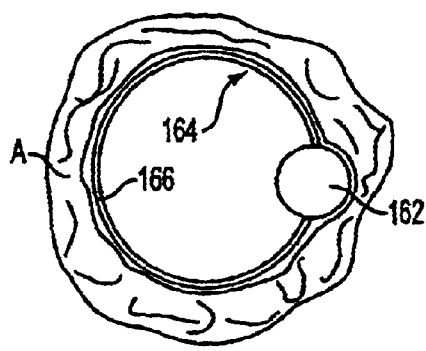

Referring to FIGS. 13A and 13B, a further alternative embodiment of the apparatus of FIG. 2 is described that may be introduced using the technique of FIG. 4, the technique of FIG. 12, or by another suitable technique. Apparatus 160 comprises catheter 162 and end effector 164. End effector 164 comprises adjustable, heatable loop 166, which is configured for dynamic sizing to facilitate positioning next to tissue at a treatment site. The size of loop 166 is adjusted so as to lie contiguous with annulus of tissue A at a treatment site, as seen in FIG. 13B. The loop may be collapsible within catheter 162 to facilitate percutaneous delivery and is electrically coupled to RF source 168, which is electrically coupled to reference electrode 170. Loop 166 may be fabricated from nitinol, copper, or any other suitably conductive and ductile material.

Figure 14A:
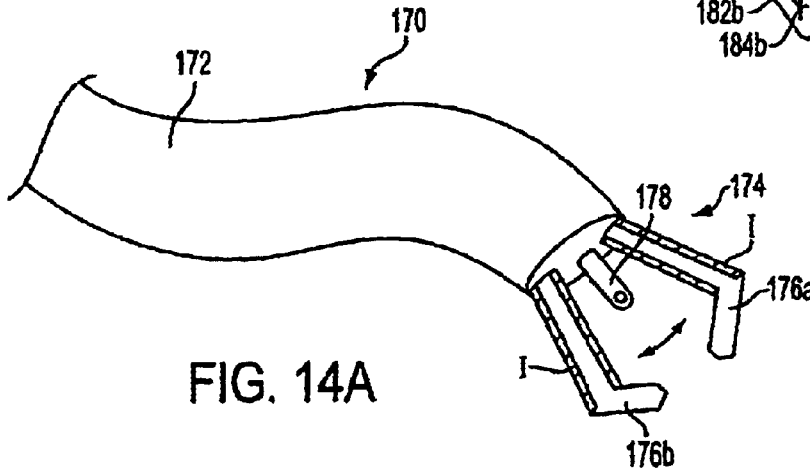
FIGS. 14A and 14B are, respectively, a side view of an alternative embodiment of the apparatus of FIG. 2, and a method of using the embodiment via the introduction technique of FIG. 12.
Figure 14B:
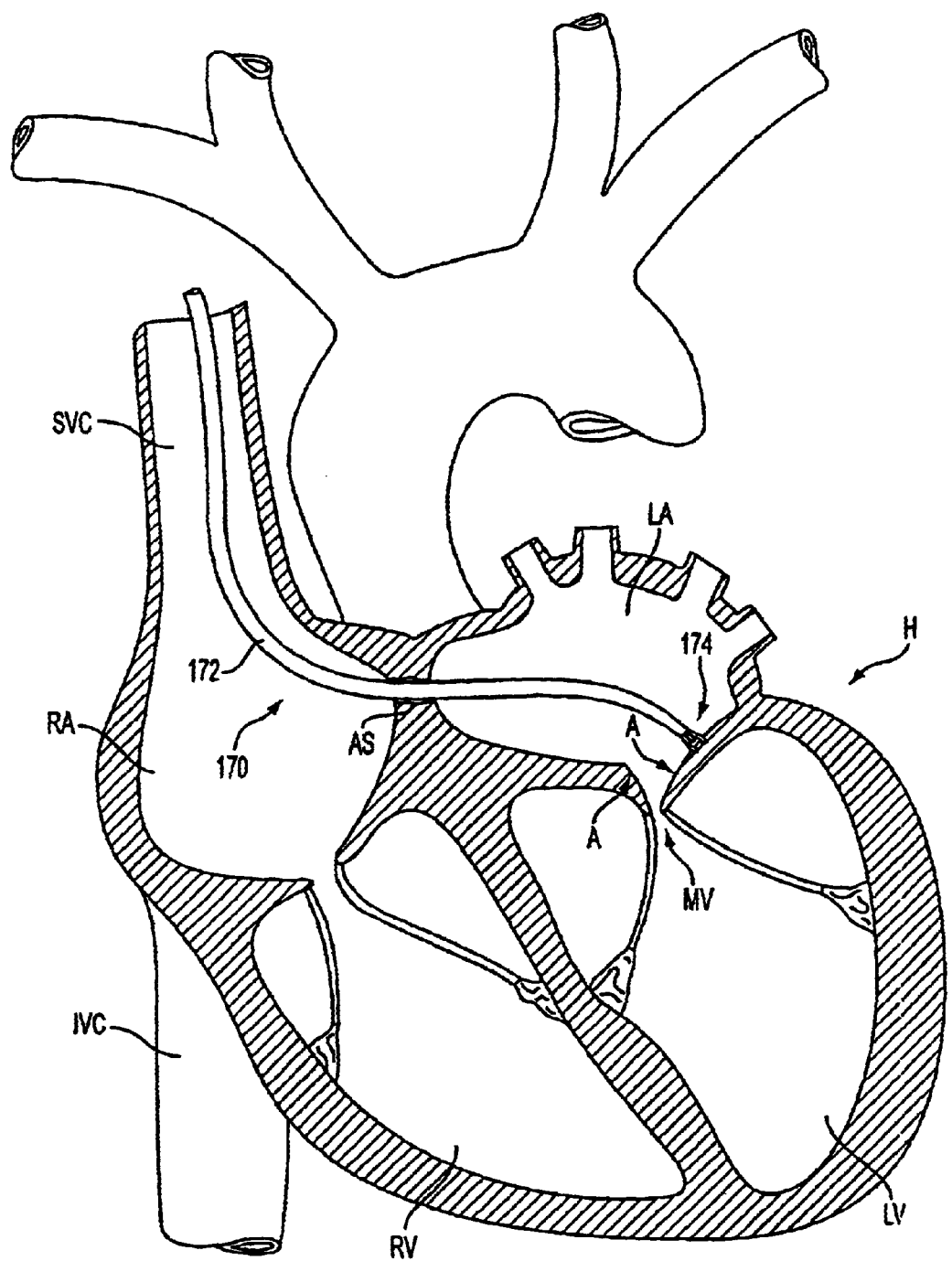

Referring to FIGS. 14A and 14B, a still further alternative embodiment of the apparatus of FIG. 2, and a method of using the embodiment with the introduction technique of FIG. 12, is described. Apparatus 170 comprises catheter 172 and end effector 174. End effector 174 is capable of grabbing and penetrating tissue, as well as delivering RF energy into tissue. End effector 174 comprises jaws 176a and 176b, which are spring-biased against one another to a closed position. By pushing a knob on the handpiece (not shown), the jaws may be actuated to an open position configured to grab tissue at a treatment site. RF energy may then be deposited in the tissue in a monopolar or bipolar mode. Jaws 176 may optionally be coated with electrically insulating layer I everywhere except in a distal region, such that tissue is only treated at depth, as described hereinabove. End effector 174 has temperature sensor 178 to control power delivered to the tissue, again as described hereinabove.

With reference to FIG. 14B, a method of using apparatus 170 via a septostomy introduction technique to treat mitral valve regurgitation is described. In particular, jaws 176 of end effector 174 are actuated to engage individual sections of valve annulus A so as to penetrate into the collagenous sublayers and to thermally shrink those sublayers. The procedure may be repeated at multiple locations around the perimeter of annulus A until regurgitation is minimized or eliminated.

Figure 15A:
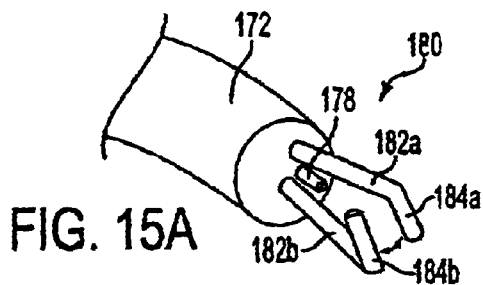
FIGS. 15A and 15B are isometric views of an alternative end effector for use with the apparatus of FIGS. 14.
Figure 15B:
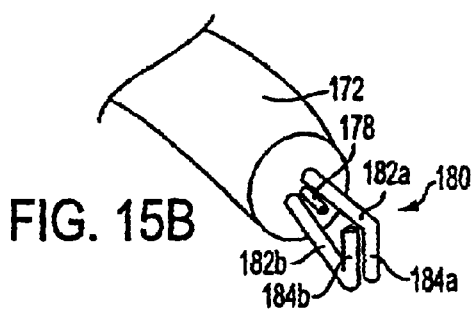

FIGS. 15A and 15B show an alternative end effector for use with apparatus 170 of FIGS. 14. End effector 180 is shown in an open position and in a closed position, respectively, and comprises jaws 182a and 182b. End effector 180 is similar to end effector 174, except that jaws 182 are configured to engage tissue with a forceps grasping motion wherein bent tips 184a and 184b of the jaws are disposed parallel to one another and contact one another when closed.

With reference now to FIGS. 16–20, apparatus of a second family of embodiments of the present invention are described. These embodiments are provided with an end effector that selectively induces a temperature rise in the chordae tendineae sufficient to cause a controlled degree of shortening of the chordae tendineae, thereby enabling valve leaflets to be properly aligned.

A preferred use for apparatus of the second family is in treatment of mitral valve regurgitation. Mitral valve regurgitation has many causes, ranging from inherited disorders, such as Marphan's syndrome, to infections and ischemic disease. These conditions affect the macromechanical condition of the mitral valve and prevent the valve from closing completely. The resulting gap in the leaflets of the valve permit blood to regurgitate from the left ventricular chamber into the left atrium.

Mechanically, the structural defects characterizing mitral valve regurgitation include: (1) the chordae tendineae are too long due to a given disease state; (2) papillary muscle ischemia changes the shape of the papillary muscle, so that attached chordae tendineae no longer pull the leaflets of the mitral valve completely shut; (3) the annulus of the mitral valve becomes enlarged, resulting in the formation of a gap between the leaflets when closed; and (4) there is an inherent weakness in the leaflets, leaving the leaflets floppy and dysfunctional.

Figure 18:
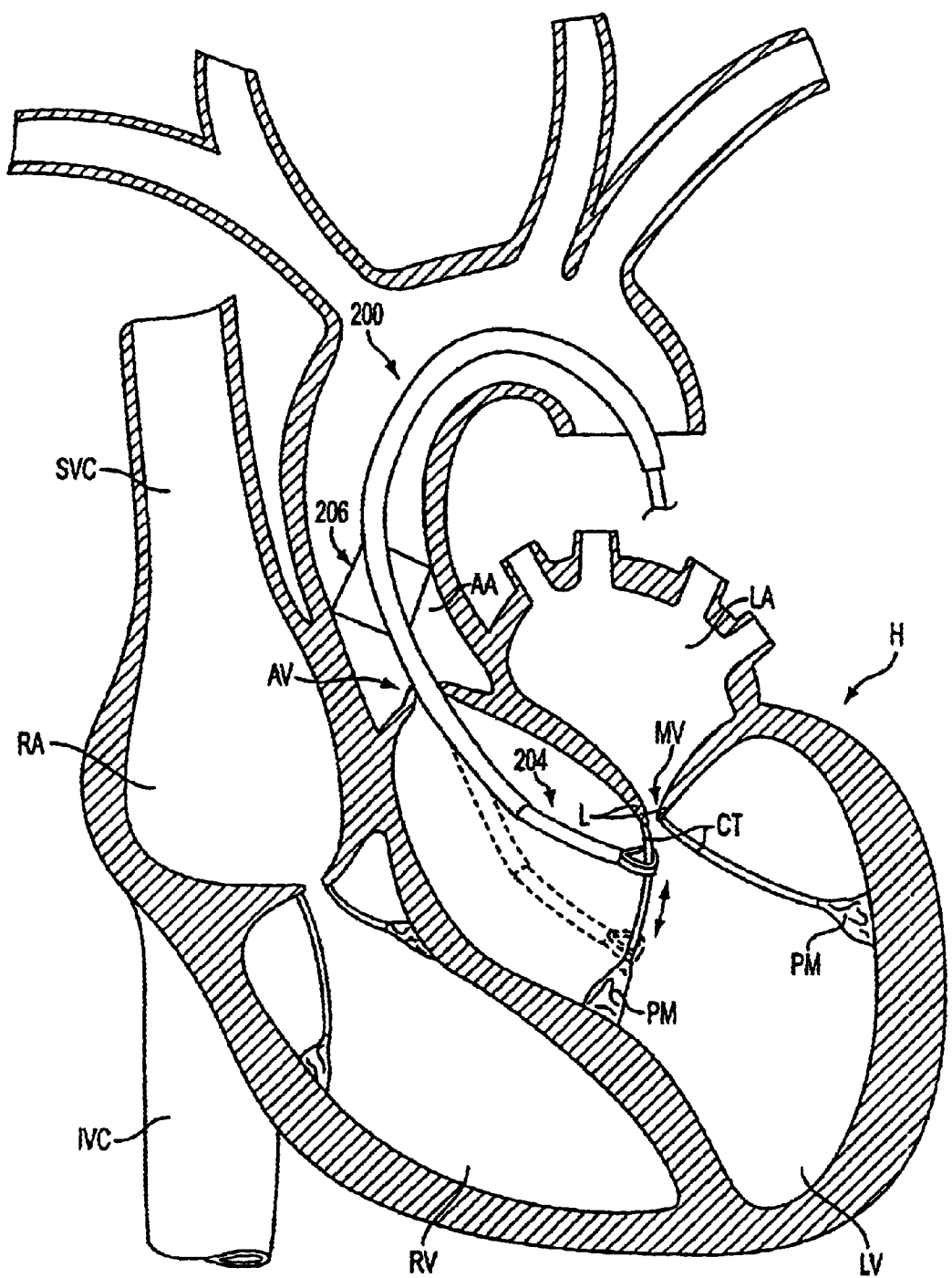
FIG. 18 is a sectional view of the human heart, illustrating a method of using the apparatus of FIG. 16 to selectively induce a temperature rise in the chordae tendineae sufficient to cause a controlled degree of shortening of the tendineae.

In accordance with the principles of the present invention, a temperature rise is induced in the support structure of the mitral valve to cause shrinkage that modifies the geometry of the valve to restore proper stopping of blood backflow and thereby regurgitation. This process is depicted in FIGS. 18–20 using the apparatus of FIGS. 16 and 17 to selectively shrink portions of the chordae tendineae, thereby bringing leaflets of the mitral valve leaflets into alignment. Apparatus of the second family may also be used in treatment of aortic valve regurgitation, and in treatment of a variety of other ailments that will be apparent to those of skill in the art.

Referring to FIG. 16, apparatus 200 comprises catheter 202 and end effector 204. Catheter 204 optionally comprises collapsible and expandable stabilizer 206, configured to stabilize apparatus 200 in a body lumen. Stabilizer 206 may comprise, for example, struts or an inflatable balloon.

End effector 204 may be collapsible to a delivery configuration within catheter 202, and may expand to a delivery configuration beyond a distal end of the catheter. End effector 204 is configured to engage, heat, and shrink chordae tendineae. Various sources of energy may be used to impart heat to the collagenous tissue and thereby shrink it, including RF energy, focused ultrasound, laser energy, and microwave energy. In addition, chemical modifiers, such as aldehydes, may be used. For laser embodiments, a preferred laser is a continuous wave Holmium:Yag laser, with application of visible or infrared laser energy in the wavelength range of 400 nanometers to 10.6 micrometers.

With reference to FIGS. 17A–17C, embodiments of end effector 204 are described. In FIG. 17A, the end effector comprises a gripping mechanism that carries the heating element. Arms 210a and 210b are opposing and spring-biased against each other. The arms may be actuated to an open position using a handpiece (not shown) coupled thereto. Arms 210a and 210b may alternatively be vertically displaced with respect to one another to allow the arms to criss-cross and tightly grasp tissue. Heating elements 212 and temperature sensors 214 are attached to the arms. Heating elements 212 may comprise electrodes, acoustic transducers, side-firing laser fibers, radioactive elements, etc. It may be desirable to employ a saline flush with heating elements 212 to prevent coagulation of blood caught between arms 210.

FIG. 17B shows an embodiment of end effector 204 with fixed, straight arms 220a and 220b. The arms are configured to engage and disengage chordae tendineae simply by being positioned against the tendineae. FIG. 17C shows an embodiment of the end effector having arms 230a and 230b. Multiple heating elements 212 are disposed on arm 230a. When heating elements 212 comprise bipolar electrodes, current flow through the tendineae using the embodiment of FIG. 17C may be achieved primarily along a longitudinal axis of the tendineae, as opposed to along a radial axis of the tendineae, as will be achieved with the embodiment of FIG. 17A. These alternative heating techniques are described in greater detail hereinbelow with respect to FIGS. 19 and 20.

Referring to FIG. 18, a method of using apparatus of the second family of embodiments to induce shrinkage of chordae tendineae CT is described. Catheter 202 of apparatus 200 is advanced percutaneously, using well-known techniques, through the ascending aorta AA and aortic valve AV into the left ventricle LV, with end effector 204 positioned within the catheter in the collapsed delivery configuration. Stabilizer 206 is then deployed to fix catheter 202 in ascending aorta AA, thereby providing a stationary leverage point.

End effector 204 is expanded to the deployed configuration distal of catheter 202. The end effector is steerable within left ventricle LV to facilitate engagement of chordae tendineae CT. End effector 204, as well as any of the other end effectors or catheters described herein, may optionally comprise one or more radiopaque features to ensure proper positioning at a treatment site. End effector 204 is capable of moving up and down the chordae tendineae to grab and selectively singe certain sections thereof, as illustrated in dotted profile in FIG. 18, to selectively shorten chordae tendineae CT, thereby treating valvular regurgitation.

When energy is transmitted through tissue utilizing one of the embodiments of this invention, the tissue absorbs the energy and heats up. It may therefore be advantageous to equip the end effector with temperature or impedance sensors, as seen in the embodiments of FIGS. 17, to output a signal that is used to control the maximum temperature attained by the tissue and ensure that the collagen or other tissues intended to be shrunk are heated only to a temperature sufficient for shrinkage, for example, a temperature in the range of 45° C.–75° C., and even more preferably in the range of 55° C.–65° C. Temperatures outside this range may be so hot as to turn the tissue into a gelatinous mass and weaken it to the point that it loses structural integrity. A closed loop feedback system advantageously may be employed to control the quantity of energy deposited into the tissue responsive to the output of the one or more sensors. In addition, the sensors may permit the clinician to determine the extent to which the cross-section of a chordae has been treated, thereby enabling the clinician to heat treat only a portion of the cross-section.

This technique is illustrated in FIGS. 19 and 20, in which alternating bands, only a single side, or only a single depth of the chordae is shrunk to leave a "longitudinal intact fiber bundle." This method may be advantageous in that, by avoiding heat treatment of the entire cross section of the chordae, there is less risk of creating mechanical weakness.

Figure 19A:
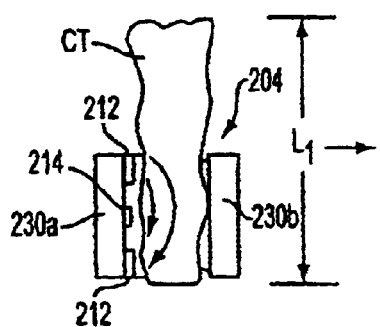
FIGS. 19A–19C show a section of chordae tendineae and illustrate a method of shrinking the tendineae in a zig-zag fashion using the end effector of FIG. 17C with the apparatus of FIG. 16.
Figure 19B:
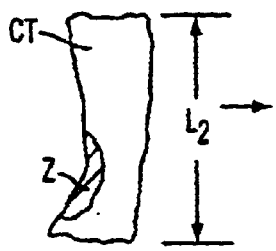
Figure 19C:
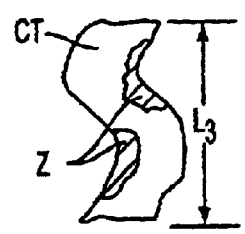

FIGS. 19A–19C depict a method of shrinking a section of chordae tendineae CT in a zig-zag fashion using the embodiment of end effector 204 seen in FIG. 17C. In FIG. 19A, the tendineae has an initial effective or straight length $L_1$. Arms 230 engage chordae tendineae CT, and heating elements 212 are both disposed on the same side of the tendineae on arm 230a. The heating elements may comprise bipolar electrodes, in which case the path of current flow through tendineae CT is illustrated by arrows in FIG. 19A.

Collagen within the tendineae shrinks, and chordae tendineae CT assumes the configuration seen in FIG. 19B. Treatment zone Z shrinks, and the tendineae assumes a shorter effective length $L_2$. Treatment may be repeated on the opposite side of the tendineae, as seen in FIG. 19C, so that the tendineae assumes a zig-zag configuration of still shorter effective length $L_3$. In this manner, successive bands of treatment zones Z and intact longitudinal fiber bundles may be established.

An additional pair of bipolar electrodes optionally may be disposed on arm 230b of the end effector to facilitate treatment in bands on opposite sides of chordae tendineae CT. The depth of shrinkage attained with apparatus 200 is a function of the distance between the electrodes, the power, and the duration of RF energy application. If, laser energy is applied, the wavelengths of energy application may be selected to provide only partial penetration of the thickness of the tissue. For example, continuous wave Holmium:YAG laser energy having a wavelength of 2.1 microns penetrates a mere fraction of a millimeter and may be a suitable energy source.

Figure 20A:
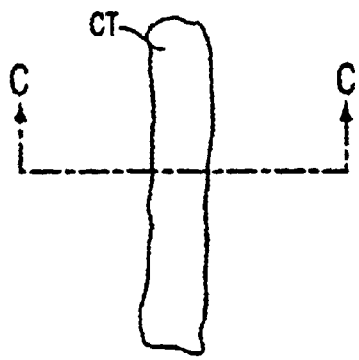
FIGS. 20A–20C show, respectively, a side view of an intact tendineae, a side view of the tendineae after treatment by a shrinkage technique, and a cross section through the tendineae along sectional view line C—C of FIG. 20A after treatment by an alternative shrinkage technique.
Figure 20B:
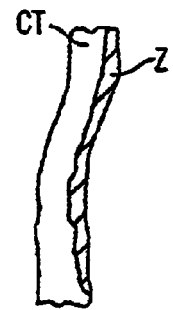
Figure 20C:
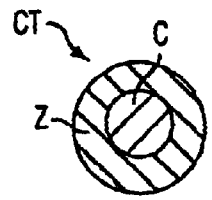

FIGS. 20A–20C illustrate additional shrinkage techniques. Intact chordae tendineae CT is seen in FIG. 20A. FIG. 20B demonstrates shrinkage with apparatus 200 only on one side of the chordae, using the technique described with respect to FIGS. 19. FIG. 20C demonstrates shrinkage with, for example the end effector of FIG. 17A or 17B, wherein, for example, bipolar current flows across the tendineae and treats the tendineae radially to a certain preselected depth. When viewed in cross-section along sectional view line C—C of FIG. 20A, chordae tendineae CT has an intact longitudinal fiber bundle core C surrounded by treatment zone Z.

With reference to FIGS. 21–22, apparatus of a third family of embodiments of the present invention are described. These embodiments are provided with an end effector comprising a mechanical reconfigurer configured to engage a longitudinal member, such as the chordae tendineae. The reconfigurer forces the longitudinal member into a tortuous path and, as a result, reduces the member's effective overall or straight length.

Figure 21A:
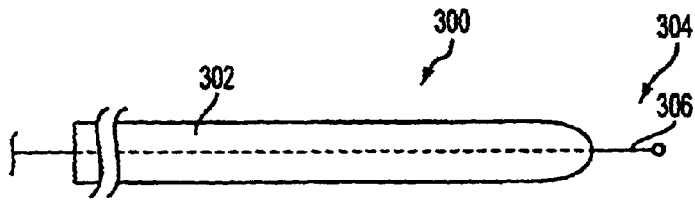
FIGS. 21A and 21B are side views of apparatus of a third family of embodiments, constructed in accordance with the present invention, shown in a collapsed delivery configuration and in an expanded deployed configuration.
Figure 21B:
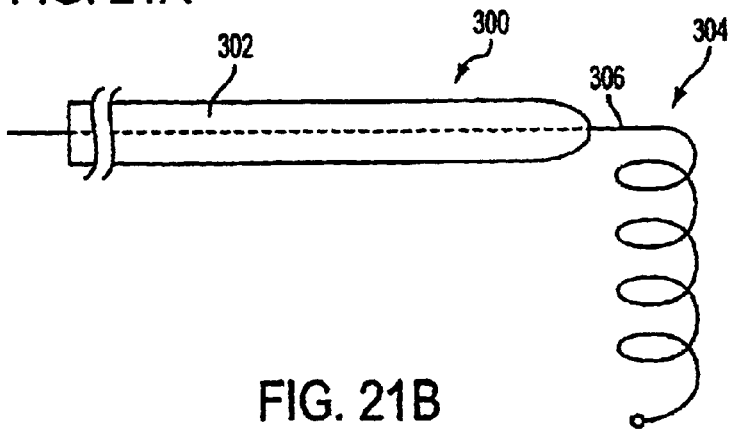

Referring to FIGS. 21A and 21B, apparatus 300 comprises catheter 302 and end effector 304. End effector 304 comprises mechanical reconfigurer 306, adapted to mechanically alter the length of a longitudinal member, for example, chordae tendineae. Reconfigurer 306 comprises a preshaped spring fabricated from a shape memory alloy, for example, nitinol, spring steel, or any other suitably elastic and strong material. Reconfigurer 306 is preshaped such that there is no straight path through its loops. Overlap between adjacent loops is preferably minimized. The shape of reconfigurer 306 causes longitudinal members, such as chordae tendineae, passed therethrough to assume a zig-zag configuration and thereby be reduced in effective length. Reconfigurer 306 is collapsible to a delivery configuration within catheter 302, as seen in FIG. 21A, and is expandable to a deployed configuration, as seen in FIG. 21B. The reconfigurer optionally may be selectively detachable from catheter 302.

Figure 22A:
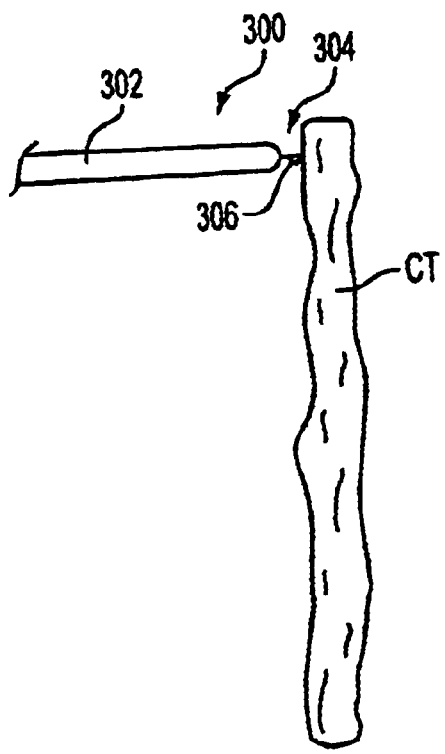
FIGS. 22A and 22B are schematic views depicting a method of using the apparatus of FIGS. 21 to mechanically shorten an effective length of chordae tendineae.
Figure 22B:
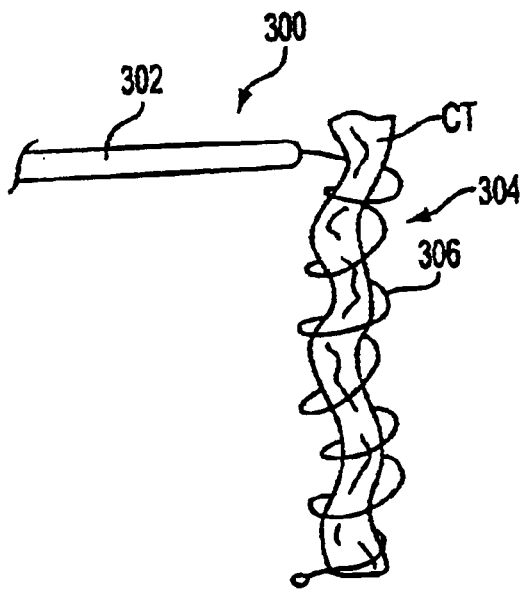

With reference to FIGS. 22A and 22B, a method of using apparatus 300 to mechanically shorten chordae tendineae CT is described. Apparatus 300 is advanced to the chordae tendineae, for example, using the technique described hereinabove with respect to FIG. 18. End effector 304 is then expanded from the delivery configuration seen in FIG. 22A to the deployed configuration of FIG. 22B. Mechanical reconfigurer 306 regains its preformed shape, and chordae tendineae CT is passed through a tortuous path that reduces its effective length, thereby treating valvular regurgitation. Reconfigurer 306 may then be detached from apparatus 300 and permanently implanted in the patient, or the reconfigurer may be left in place for a limited period of time to facilitate complementary regurgitation treatment techniques.

Other embodiments of the third family in accordance with the present invention will be apparent to those of skill in the art in light of this disclosure.

Figure 23:
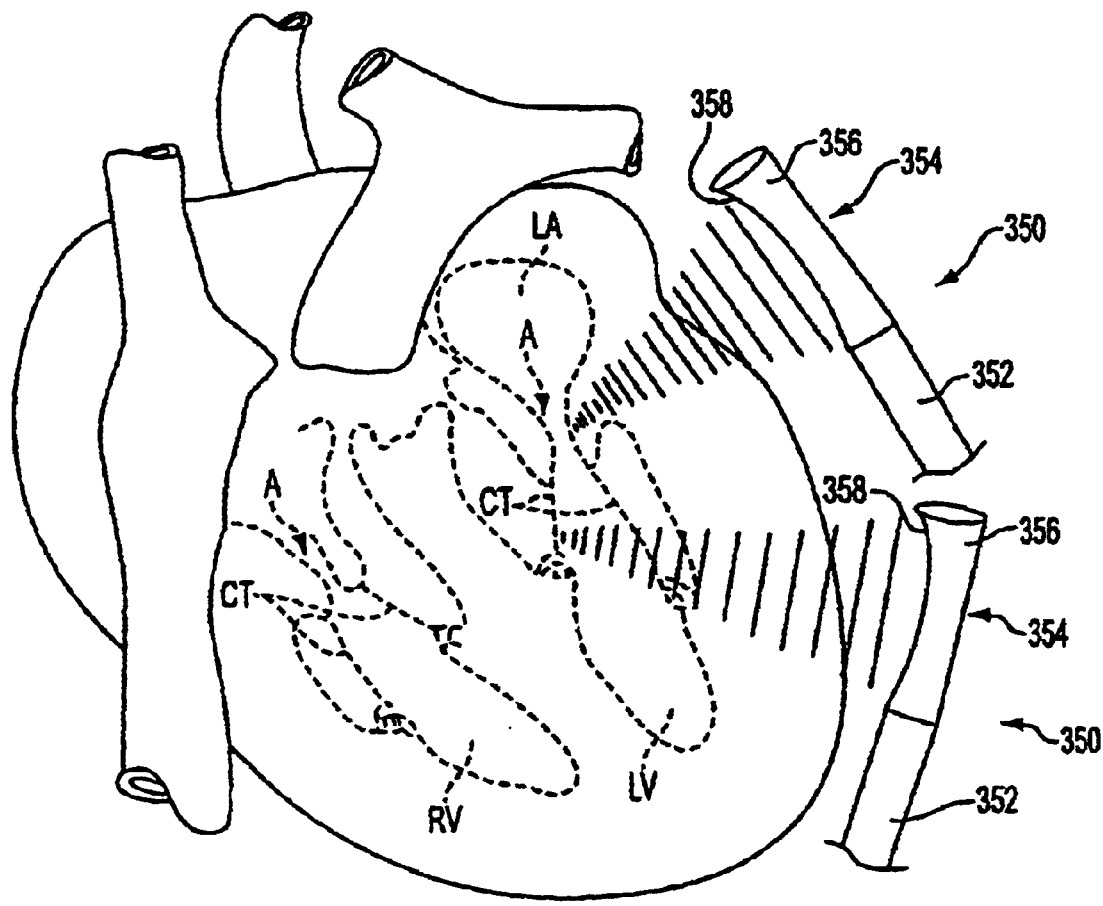
FIG. 23 is a side view, partially in section, illustrating a method and apparatus for non-invasive coagulation and shrinkage of scar tissue in the heart, or shrinkage of the valve structures of the heart.

Referring now to FIG. 23, apparatus in accordance with the present invention is described that may be used as either an embodiment of the first family or of the second family. Apparatus and methods are provided for noninvasively coagulating and shrinking scar tissue around the heart, or valve structures inside the heart, using energy delivered via high intensity, focused ultrasound. Apparatus 350 comprises catheter 352 and end effector 354. End effector 354 comprises ultrasonic transducer 356 and focusing means 358, for example, a lens. Focused ultrasound is propagated and directed with a high level of accuracy at the chordae CT, the annuluses A of the valves or at a section of bulging wall of the heart, using, for example, echocardiography or MRI for guidance. As with the previous embodiments, the shrinkage induced by energy deposition is expected to reduce valvular regurgitation. Apparatus 350 may also be used to reduce ventricular volume and shape, in cases where there is bulging scar tissue on the wall of the left ventricle LV secondary to acute myocardial infarction.

All of the above mentioned methods and apparatus may be used in conjunction with flow-indicating systems, including, for example, color Doppler flow echocardiography, MRI flow imaging systems, or laser Doppler flow meters. Application of energy from the end effector may be selected such that regurgitation stops before the procedure is completed, as verified by the flow-indicating system. Alternatively, the procedure may be "overdone" to compensate for expected tissue relapse, without compromising the ultimate outcome of the procedure.

Additionally, all of the foregoing apparatus and methods optionally may be used in conjunction with ECG gating, thereby ensuring that tissue is at a specified point in the cardiac cycle before energy is deposited into the tissue. ECG gating is expected to make treatment more reproducible and safer for the patient.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. Apparatus for treating tissue at a target site to modify flow through a valve, the apparatus comprising:
   a catheter having a distal end region, the catheter configured for transluminal delivery of the end region to the target site; and
   an end effector in communication with the distal end region, the end effector configured to approximate the shape of the tissue while transferring energy to the tissue at the target site to induce thermal shrinkage of collagen in the tissue, thereby modifying flow through the valve by reducing a circumference of the valve.

2. The apparatus of claim 1, wherein the tissue at the target site comprises an annulus of tissue surrounding a cardiac valve.

3. The apparatus of claim 2, wherein modifying flow through the valve comprises reducing a circumference of the cardiac valve.

4. The apparatus of claim 1, wherein the tissue at the target site comprises a support structure of a cardiac valve.

5. The apparatus of claim 4, wherein the support structure is chosen from the group consisting of a chordae tendineae and a papillary muscle.

6. The apparatus of claim 5, wherein modifying flow through the valve comprises shortening the chordae tendineae to properly align leaflets of the valve.

7. The apparatus of claim 1, wherein the tissue at the target site comprises a leaflet of a cardiac valve.

8. The apparatus of claim 1 wherein the end effector comprises a temperature sensor.

9. The apparatus of claim 8, wherein the temperature sensor is configured to penetrate tissue.

10. The apparatus of claim 1, wherein the end effector comprises a tissue heating element.

11. The apparatus of claim 9, wherein the tissue heating element is chosen from the group consisting of a monopolar electrode, a pair of bipolar electrodes, an acoustic transducer, a laser fiber coupled to a laser source, and a radiation source.

12. The apparatus of claim 10, wherein the monopolar electrode is coupled to an RF source and a reference electrode.

13. The apparatus of claim 10, wherein an RF source is coupled between the pair of bipolar electrodes.

14. The apparatus of claim 1, wherein the end effector has a collapsed delivery configuration within a lumen of the catheter, and an expanded deployed configuration extending out of the lumen.

15. The apparatus of claim 14, wherein the end effector is configured to penetrate tissue at the target site in the deployed configuration.

16. The apparatus of claim 15, wherein the end effector further comprises an electrically insulating coating everywhere except at its distal end.

17. The apparatus of claim 16, wherein the end effector is configured to approximate the shape of an annulus in the deployed configuration.

18. The apparatus of claim 1, wherein the end effector comprises coolant to minimize surface tissue damage at the target site.

19. The apparatus of claim 1, wherein the end effector comprises a saline flush.

20. The apparatus of claim 1, wherein the catheter further comprises a stabilizer configured to stabilize the catheter within a body lumen.

21. The apparatus of claim 1, wherein the end effector is configured to engage tissue.

22. The apparatus of claim 1, wherein the end effector comprises an expandable balloon.

23. The apparatus of claim 1, wherein the end effector comprises a wrapped sheet.

24. The apparatus of claim 1, wherein the end effector comprises an atraumatic tipped leg.

25. The apparatus of claim 1, wherein the end effector comprises a mechanical reconfigurer.

26. The apparatus of claim 1, wherein the end effector comprises barbs.

27. The apparatus of claim 1, wherein the end effector comprises an adjustable, heatable loop.

28. The apparatus of claim 1, wherein the end effector comprises jaws.

29. The apparatus of claim 1, wherein the end effector comprises arms.

30. The apparatus of claim 1, further comprising a flow-indicating system in communication with the end effector.

31. The apparatus of claim 30, wherein the flow-indicating system is chosen from the group consisting of a color Doppler flow echocardiography system, an MRI flow imaging system, and a laser Doppler flow meter.

32. The apparatus of claim 1, further comprising an ECG gating system in communication with the end effector.

33. A method for altering flow through a valve, the method comprising:
   providing apparatus comprising a catheter having a distal end region, and an end effector in communication with the end region;
   transluminally positioning the end effector in communication with tissue at a treatment site in the vicinity of the valve such that the end effector approximates a shape of the tissue; and
   transferring energy from the end effector to the tissue at the treatment site to shrink collagen in the tissue, thereby altering flow through the valve by reducing a circumference of the valve.

34. The method of claim 33, wherein the treatment site is chosen from the group consisting of an annulus of tissue surrounding a cardiac valve, a support structure of a cardiac valve, a leaflet of a cardiac valve, a chordae tendineae of a cardiac valve, a papillary muscle, a urinary sphincter, a digestive system valve, and a leg vein valve.

35. The method of claim 33, wherein transferring energy from the end effector to the tissue comprises transferring radiofrequency energy to the tissue.

36. The method of claim 33, wherein transferring energy from the end effector to the tissue comprises transferring acoustic energy to the tissue.

37. The method of claim 33, wherein transferring energy from the end effector to the tissue comprises transferring laser energy to the tissue.

38. The method of claim 37, wherein the laser energy has a wavelength in a range of 400 nanometers to 10.6 micrometers.

39. The method of claim 38, wherein the laser energy is provided by a continuous wave Holmium:YAG laser.

40. The method of claim 33, wherein transferring energy from the end effector to the tissue comprises transferring radioactive energy to the tissue.

41. The method of claim 33, wherein transferring energy from the end effector to the tissue comprises transferring chemical energy to the tissue.

42. The method of claim 33, wherein transferring energy from the end effector to the tissue comprises transferring mechanical energy to the tissue.

43. The method of claim 33, wherein transferring energy from the end effector to the tissue comprises elevating a temperature of the tissue to a temperature within a range of 45° C.–75° C.

44. The method of claim 33, wherein transluminally positioning the end effector comprises percutaneously advancing the apparatus through a patient's venous vasculature.

45. The method of claim 33, wherein transluminally positioning the end effector comprises percutaneously advancing the apparatus through a patient's arterial vasculature.

46. The method of claim 33, wherein transluminally positioning the end effector comprises performing a septostomy.

47. The method of claim 33, further comprising synchronizing energy transfer with a repetitive point in a patient's cardiac cycle.

48. The method of claim 33, further comprising monitoring flow through the valve during energy transfer.

* * * * *